United States Patent
Flinner et al.

(10) Patent No.: US 7,836,710 B2
(45) Date of Patent: Nov. 23, 2010

(54) FREEZER WITH DEFROSTING INDICATOR

(75) Inventors: Klaus Flinner, Zöschingen (DE); Georg Hausmann, Dillingen (DE); Stefan Holzer, Aalen (DE); Fritz Hägele, Herbrechtingen (DE); Helmut Konopa, Leipheim (DE); Jörg Stelzer, Giengen/Brenz (DE)

(73) Assignee: BSH Bosch und Siemens Hausgeraete GmbH, Munich (DE)

( * ) Notice: Subject to any disclaimer, the term of this patent is extended or adjusted under 35 U.S.C. 154(b) by 686 days.

(21) Appl. No.: 10/989,809

(22) Filed: Nov. 16, 2004

(65) Prior Publication Data

US 2005/0120727 A1    Jun. 9, 2005

Related U.S. Application Data

(63) Continuation of application No. PCT/EP03/05081, filed on May 14, 2003.

(30) Foreign Application Priority Data

May 16, 2002    (DE) ................ 102 21 903

(51) Int. Cl.
  *F25D 21/02*    (2006.01)
  *F25B 49/00*    (2006.01)
  *G01K 13/00*    (2006.01)

(52) U.S. Cl. .................. 62/128; 62/126; 62/129; 62/140

(58) Field of Classification Search .......... 62/126, 62/127, 150, 140, 89, 129, 158, 213, 128; 374/162
See application file for complete search history.

(56) References Cited

U.S. PATENT DOCUMENTS

| | | | | |
|---|---|---|---|---|
| 1,945,100 | A * | 1/1934 | Troll | 62/128 |
| 4,074,987 | A * | 2/1978 | Krulewich | 62/128 |
| 4,176,524 | A * | 12/1979 | Kamiyama et al. | 62/140 |
| 4,348,869 | A * | 9/1982 | Massa | 62/140 |
| 4,578,959 | A * | 4/1986 | Alsenz | 62/140 |
| 4,831,833 | A | 5/1989 | Duenes et al. | |
| 5,483,804 | A * | 1/1996 | Ogawa et al. | 62/153 |
| 5,522,232 | A * | 6/1996 | Nojiri | 62/140 |
| 5,564,286 | A * | 10/1996 | Suse | 62/153 |
| 5,887,443 | A * | 3/1999 | Lee et al. | 62/153 |
| 6,622,497 | B2 | 9/2003 | Marques et al. | |
| 2001/0054292 | A1 * | 12/2001 | Davis et al. | 62/154 |
| 2003/0074906 | A1 | 4/2003 | Marques et al. | |

FOREIGN PATENT DOCUMENTS

| | | |
|---|---|---|
| EP | 0 563 751 A1 | 10/1993 |
| EP | 0 644 386 A1 | 3/1995 |
| JP | 08136092 A | 5/1996 |
| WO | 01/51865 A1 | 7/2001 |

* cited by examiner

*Primary Examiner*—Chen-Wen Jiang
(74) *Attorney, Agent, or Firm*—James E. Howard; Andre Pallapies

(57) ABSTRACT

A freezer includes a refrigerating surface that is capable of freezing and a measuring circuit for estimating the quantity of ice located on the refrigerating surface and for furnishing a warning signal when the estimated quantity of ice exceeds a limit value. The freezer includes a sensor sensing at least one climatic condition and a refrigerating surface periodically freezing, and a measuring circuit having at least one sensor and a time measuring device estimating a quantity of ice on said refrigerating surface based upon various factors. A warning signal is supplied when an estimated quantity of ice exceeds a predetermined limit value.

2 Claims, 4 Drawing Sheets

FREEZER WITH DEFROSTING INDICATOR

CROSS-REFERENCE TO RELATED APPLICATION

This is a continuing application, under 35 U.S.C. §120, of copending international application No. PCT/EP03/05081, filed May 14, 2003, which designated the United States; this application also claims the priority, under 35 U.S.C. §119, of German patent application No. 102 21 903.6, filed May 16, 2002; the prior applications are herewith incorporated by reference in their entirety.

BACKGROUND OF THE INVENTION

Field of the Invention

The present invention relates to a freezer, such as, for instance, a freezer cabinet, a chest freezer, or a combined refrigerator-freezer.

For cooling the interior space, such freezers have an evaporator that, under normal operating conditions, is at temperatures below 0° C. and on which moisture from the interior space is precipitated. In the course of operation of the refrigerator, the moisture may form a crust of ice, which, as the thickness increases, increasingly impairs the efficiency of the evaporator.

To prevent the formation of an excessively thick layer of ice on the evaporator, so-called no-frost appliances have been developed. In such appliances, the evaporator is automatically defrosted—usually under time control. This is possible without the refrigerated items warming up to any appreciable extent because the evaporator is accommodated in a chamber that is separate from the storage space for the refrigerated items of the refrigerator and the storage space is cooled by air circulating between it and the chamber of the evaporator. By switching off the circulation, the heat exchange between the evaporator chamber and the storage space can be reduced considerably for a time. As such, it is possible to heat the evaporator in the chamber for defrosting, without this, at the same time, leading to undesired warming up of the refrigerated items.

So-called static freezers, i.e., freezers without automatic defrosting, may in comparison have a more simple construction because the evaporator can be mounted directly on the storage space for the refrigerated items. Also a device for air circulation is not required. Static freezers are, therefore, generally less expensive to buy than comparable appliances with an automatic no-frost system and, because they eliminate the need for heating, they also seemingly have better energy efficiency than the latter so that some users prefer them over no-frost appliances.

However, the seemingly better energy efficiency of the static freezers can easily change over to the opposite situation if they are not defrosted sufficiently frequently. Because the defrosting of a static freezer is a labor-intensive operation—the refrigerated items contained in it must be unloaded, temporarily stored with thermal insulation and be re-loaded again after defrosting—and the users generally have no possible way of establishing exactly the optimum defrosting time, the users tend to defrost rarely.

SUMMARY OF THE INVENTION

It is accordingly an object of the invention to provide a freezer with defrosting indicator that overcomes the hereinafore-mentioned disadvantages of the heretofore-known devices of this general type and that makes it easier for the user to identify the optimum defrosting time.

With the foregoing and other objects in view, there is provided, in accordance with the invention, a freezer, including a housing having a refrigerating surface at least periodically freezes during operation and a measuring circuit estimating a quantity of ice on the refrigerating surface and supplying a warning signal when an estimated quantity of ice exceeds a predetermined limit value.

In accordance with another feature of the invention, the freezer is equipped with a built-in indicating element that can be activated by the warning signal. The indicating element is, preferably, an optical indicating element because a user can ignore an optical warning signal more readily than an acoustic warning signal for a while until the user has time to defrost the appliance without being excessively bothered by the signal.

In accordance with a further feature of the invention, alternatively or additionally, the freezer may also be equipped with an interface for transmitting the warning signal into a data network to be able to indicate the warning signal also at a data terminal remote from the freezer.

In accordance with an added feature of the invention, one possible way of estimating the quantity of ice located on the refrigerating surface is that of direct measurement; for such a purpose, the measuring circuit may include at least one ice sensor for sensing the presence or the layer thickness of ice on the refrigerating surface. Such sensors may be based on optical principles, for example, they may use total internal reflection properties of a transparent surface portion on the refrigerating surface that are changed by a coating of ice. Acoustic measuring principles are also conceivable; for example, the resonant frequency, changed by a coating of ice, of a mechanical oscillator disposed on the refrigerating surface may be sensed and evaluated.

Indirect estimation of the ice coverage by measuring parameters that are not necessarily associated with the ice coverage but are associated with it with sufficient probability is also possible. In accordance with an additional feature of the invention, a simple, inexpensive possibility is, for example, that the measuring circuit includes a time measuring device, and that the necessity for defrosting is assumed when a time measured by the time measuring device because a fixed point in time has exceeded a limit value. The time at which the freezer was put into operation since the last defrosting operation may, generally, be taken as this fixed point in time.

In accordance with yet another feature of the invention, in the simplest case, the time measured by the time measuring device may be the overall operating time of the freezer since the fixed point in time.

In accordance with yet a further feature of the invention, the time measuring device merely measures the time that the door of the refrigerator has been left open since the fixed point in time. Such a measurement permits a more precise estimation of the quantity of ice because it is substantially the case that moisture that is precipitated on the refrigerating surface as ice can only be introduced into the interior of the freezer while the door is left open.

In accordance with yet an added feature of the invention, another possibility is to use the time measuring device for measuring the running time of a compressor of the freezer since the fixed point in time.

In accordance with yet an additional feature of the invention, another simple possibility is that, instead of measuring the time for which the door has been left open, the measuring circuit measures the number of times the door has been opened and detects the necessity for defrosting when this number exceeds a limit value.

In accordance with again another feature of the invention, an operating element, which can be actuated by a user for establishing the fixed point in time mentioned above, and also measures for storing the state of the measuring circuit in a de-energized state of the freezer are provided on the freezer. With the aid of these storage devices, state parameters of the measuring circuit, such as, for instance, the limit value, a measured time, the number of door openings, or the like, can be saved during a de-energized state of the freezer so that a brief power failure does not lead to re-setting of the measuring circuit or of the values sensed by it.

Because these storage measures also store the state of the measuring circuit when the appliance is switched off for defrosting, the operating element is required for re-establishing the fixed point in time.

In accordance with again a further feature of the invention, to improve the estimation of the quantity of ice, the measuring circuit may be equipped expediently with a sensor that senses at least one climatic condition in the ambience of the freezer. The sensing result can be used to establish the limit value in dependence on it, to weight the time measured by the time measuring device with a factor dependent on the sensed climatic condition or, else, to weight each door opening with such a factor. The ambient temperature or ambient atmospheric humidity is suitable as a climatic condition.

In accordance with again an added feature of the invention, the measuring circuit includes a time measuring device for measuring the running time of a compressor of the freezer and is set up to estimate the quantity of ice based upon the ratio of the running time of the compressor to its idle time or to the overall operating time of the freezer.

With the objects of the invention in view, there is also provided a freezer, including a housing having a refrigerating surface at least periodically freezes during operation; and a measuring circuit programmed to estimate a quantity of ice on the refrigerating surface and to supply a warning signal when an estimated quantity of ice exceeds a predetermined limit value.

Other features that are considered as characteristic for the invention are set forth in the appended claims.

Although the invention is illustrated and described herein as embodied in a freezer with defrosting indicator, it is, nevertheless, not intended to be limited to the details shown because various modifications and structural changes may be made therein without departing from the spirit of the invention and within the scope and range of equivalents of the claims.

The construction and method of operation of the invention, however, together with additional objects and advantages thereof, will be best understood from the following description of specific embodiments when read in connection with the accompanying drawings.

DESCRIPTION OF THE PREFERRED EMBODIMENTS

Figure 1:
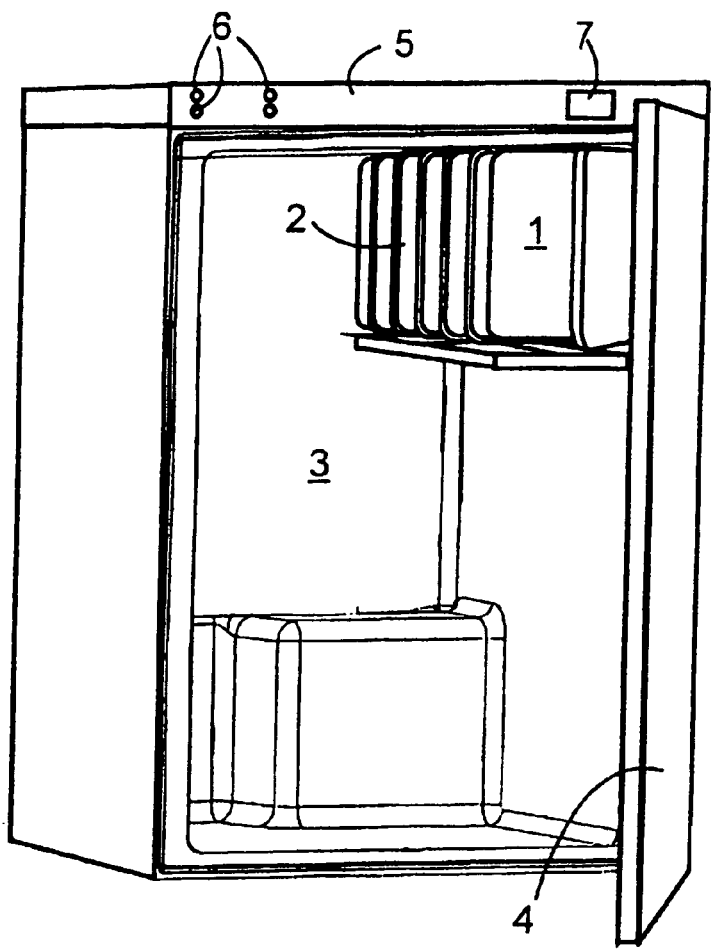
FIG. 1 is a perspective view of a freezer according to the invention.

Referring now to the figures of the drawings in detail and first, particularly to FIG. 1 thereof, there is shown a refrigerator with a built-in freezing compartment 1. An evaporator 2 forms the outer wall of the freezing compartment 1, which delimits the compartment 1 from a refrigerating compartment 3, which fills the greater part of the interior space of the refrigerator. Disposed above the door 4 on the housing of the refrigerator is an operating panel 5, which has various switches and/or controllers 6 for setting the function of the refrigerator and also an indicating element 7, for example, an LED or LCD indicator. Electronic circuits for controlling the operation of the refrigerator in dependence on settings performed by a user at the switches 6 are accommodated behind the operating panel.

Figure 2:
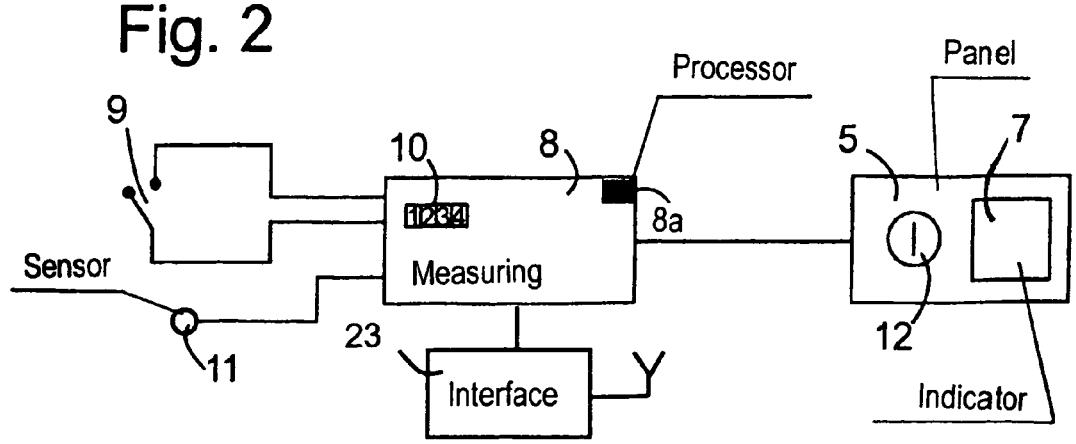
FIG. 2 is a block and schematic circuit diagram of a measuring circuit and circuit elements connected thereto the freezer according to FIG. 1.

These electronic circuits include a measuring circuit 8, which is schematically shown in FIG. 2. The measuring circuit 8 can be operated with or controlled by a microprocessor 8a that is programmed to carry out instructions for performing the methods according to the invention.

Figure 3:
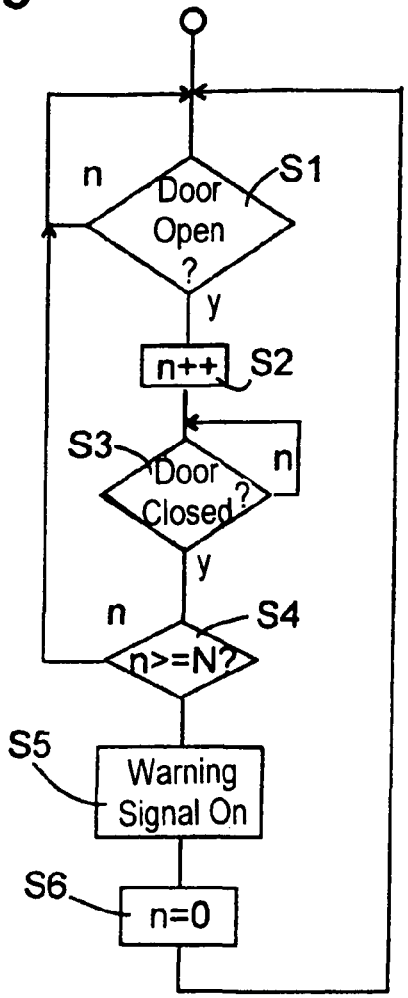
FIG. 3 is a flow diagram of a first embodiment of a method according to the invention performed with the measuring circuit of FIG. 2.

In a simple refinement of the invention, the measuring circuit 8 is connected, on one hand, to a switch 9, which is actuated by opening and closing of the door 4. Such a switch 9 is present conventionally in refrigerators for switching the illumination of the interior space. The measuring circuit 9 includes a counter 10 for counting the number of times that the door 4 is opened. Furthermore, the measuring circuit 8 is connected to the indicator 7. A working method of this simple refinement of a measuring circuit is shown in FIG. 3.

The elements 11, 12 shown in FIG. 2 are not required in the case of this simple refinement and are explained later.

When the refrigerator is switched on, the counter 10 has the value zero. In step S1 of the method, the measuring circuit monitors the state of the door 4; as long as the door 4 is closed, nothing happens; if the door 4 is opened, the content n of the counter is incremented by 1 in step S2. Once it has been established in step S3 that the door 4 has been closed again, the measuring circuit 8 compares n with a predetermined limit value N. If n<N, the method returns to step S1; if n≧N, a warning signal is activated in step S5. This may happen, for example, by switching on an element of the indicator 7 that is specially provided for such a purpose. However, the indicator 7 may also be, for example, a digital indicator, which serves, for example, for indicating a temperature measured by a temperature sensor in the interior of the refrigerator and that, to represent the warning signal, is switched over from a continuous indicating mode to a flashing mode.

If the user acknowledges the warning signal and switches off the refrigerator to defrost it, the counting value stored in the counter 10 is lost or reset so that the counter 10 receives the value zero when the refrigerator is put into operation again.

The freezer may also be equipped with an interface 23 for transmitting the warning signal into a data network so that the warning signal can be indicated at a data terminal remote from the freezer.

Figure 3A:
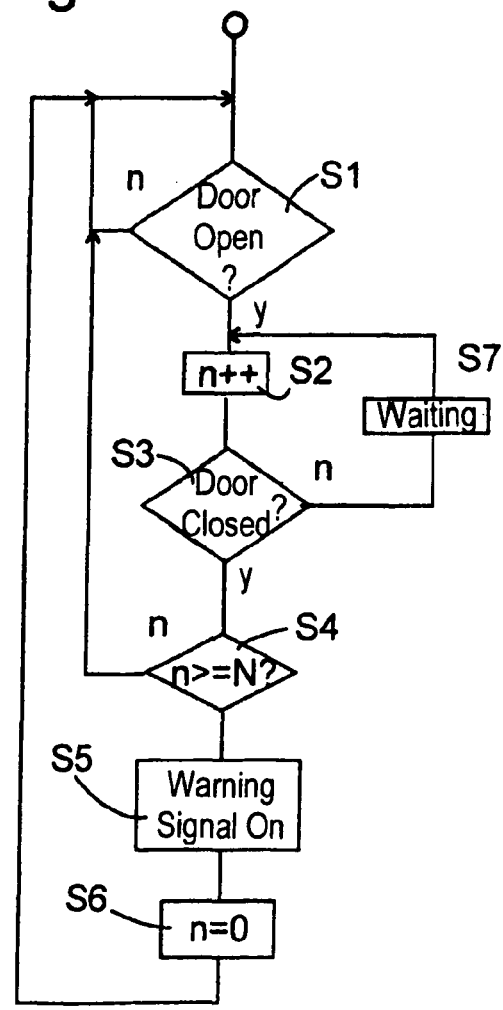
FIG. 3A is a flow diagram of a second embodiment of a method according to the invention performed with the measuring circuit of FIG. 2.

FIG. 3A shows a modification of the method from FIG. 3. For such a modification, the measuring circuit 8 expediently includes a time measuring device, such as, for instance, a monostable multivibrator. Each time it is established in step S3 that the door 4 is open, the time measuring device is activated to measure a predetermined time interval and, during this interval, pauses the processing. After expiry of the time interval, the counting value n is once again incremented. The counting value here does not indicate the number of times the door has been opened since the last defrosting, but is a measure of the time for which the door 4 has been left open since then.

Alternatively, in FIGS. 3 and 3A, steps S2 and S4, checking whether or not the door has been left open, could be replaced by checking whether or not the compressor of the refrigerator is running. In such a case, the counting value n is a measure of how often the compressor has been switched on since the last defrosting or how long it has been running since then.

In a further-developed refinement of the freezer, the measuring circuit 8 is additionally connected to a sensor 11 for sensing the atmospheric humility and/or the temperature of the air in the ambience of the refrigerator and/or to a resetting switch 12 on the operating panel 5. In this refinement, the counter 10 is non-volatile, i.e., a numerical value stored therein is retained in the event of failure of the supply voltage of the refrigerator.

Figure 4:
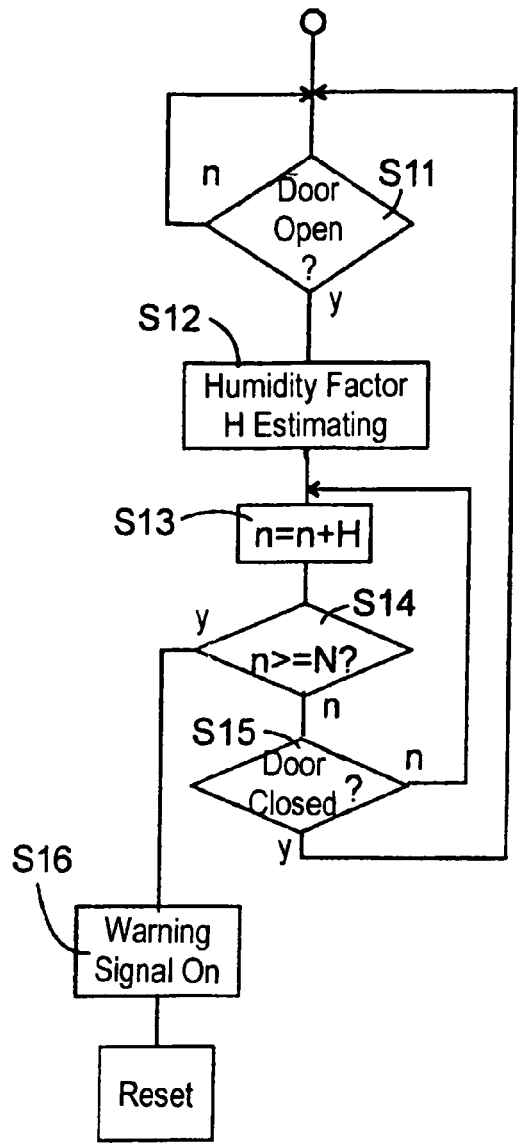
FIG. 4 is a flow diagram of a third embodiment of a method according to the invention performed with the measuring circuit of FIG. 2.

FIG. 4 shows an example of a working method of the measuring circuit according to this refinement. The method begins, like that of FIG. 3, with the measuring circuit waiting in step S11 for the door 4 to be opened. If the door 4 has been opened, the measuring circuit 8 estimates, in step S12, a humidity factor H based upon the measured results supplied by the sensor 11, the humidity factor H is intended to represent a measure of the amount of moisture that is introduced into the refrigerator when the door is opened. In the ideal case, this humidity factor H is proportional to the absolute moisture content of the ambient air; this presupposes that both the relative atmospheric humidity and the temperature of the ambient air are measured with the aid of the sensor 11. If the sensor 11 measures only one of these two variables, the humidity factor determined therefrom can, at most, be correlated with the actual introduction of moisture, but this is not sufficient for the purposes of the invention.

In step S13, the counting value n in the counter 10 is incremented by the humidity factor H, and, subsequently, in step S14, a check is made to determine whether or not the limit value N has been exceeded. If this is not the case, and it is also established after a predetermined time period in step S15 that the door is still open, the method returns to step S13. As such, the counter 10 is incremented at regular time intervals as long as the door 4 is open. If, however, it is established that the door 4 is closed, the method returns to step S11, in which the circuit waits for renewed opening of the door 4.

If the check performed in step S14 shows that the limit value N has been exceeded, the warning signal is switched on.

Because, in the refinement considered here, the content of the counter 10 is not lost when the refrigerator is switched off for defrosting, the user must actuate the resetting switch 12 to reset the content of the counter 10 to zero when the appliance is put into operation again after defrosting.

As an alternative to the refinements described above, it is, of course, also possible for the content of the counter 10 to be set to N when the refrigerator is put into operation again or the resetting switch 12 is actuated, for the incrementation in step S2 or step S13 to be replaced by a decrementation and a critical thickness of the ice on the evaporator, necessitating defrosting, to be regarded as reached when the counter 10 reaches the value zero.

Figure 5:
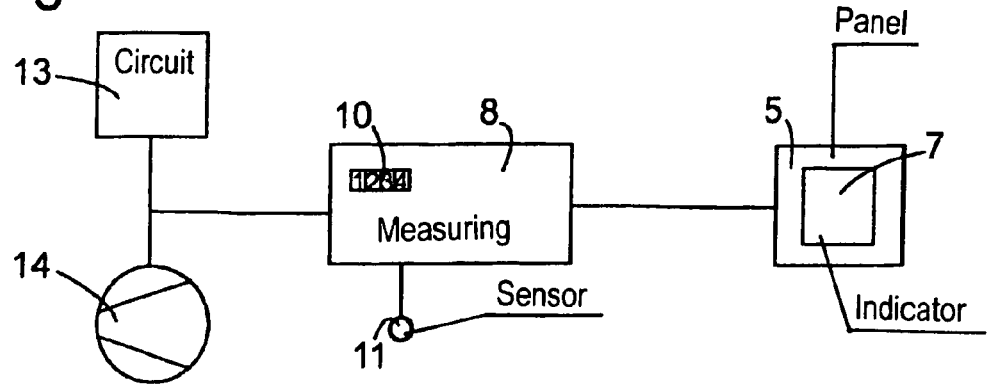
FIG. 5 is a block and schematic circuit diagram of an alternative embodiment of the measuring circuit according to the invention and circuit elements connected there of a freezer according to the invention.

In a refinement of the invention schematically represented in FIG. 5, an input of the measuring circuit 8 is connected to an output of a thermostat circuit 13. The thermostat circuit 13 supplies a signal for switching on or off the compressor 14 of the refrigerating machine of the refrigerator in dependence on a temperature measured in its interior. The length of the running phases of the compressor 14 in relation to the overall operating time of the refrigerator is dependent, on one hand, on the temperature difference maintained between the interior space of the refrigerator and its ambience and, on the other hand, on the effectiveness of the evaporator 2. That is to say—the running phases of the compressor 14 required for maintaining a given temperature in the interior space of the refrigerator are all the longer when the layer of ice on the evaporator 2 is thicker, which insulates the latter from the interior space. The measuring circuit 8 determines a sliding mean value of the ratio of the duration of the running phases to the duration of the overall operating time and supplies the warning signal when such a ratio exceeds a predetermined limit value. It is also optionally possible, in this refinement, for an ambient temperature sensor 11 to be provided to make it possible for the measuring circuit 8 to choose the limit value in dependence on the ambient temperature and, as such, compensate at least partially for the dependence of the duration of the running phases on the temperature difference to be maintained.

Figure 6:
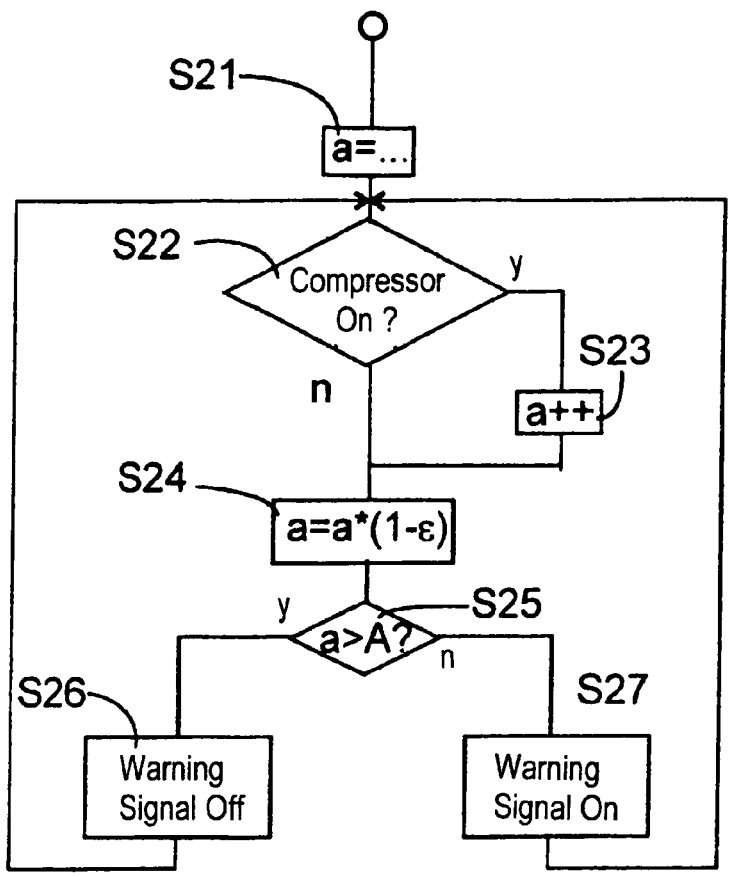
FIG. 6 is a flow diagram of a method according to the invention performed with the measuring circuit of FIG. 5.

FIG. 6 shows an example of a possible working method of the measuring circuit 8 from FIG. 5. After the refrigerator is switched on, the method begins in step S21 by initializing the counting value a in the counter 10 (which may be a real number here and is intended to represent a measure of the ratio of the compressor running time to the overall running time of the refrigerator) to a value below a predetermined limit value A—if appropriate, selected temperature-dependently. If it is subsequently found in step S22 that the compressor is switched on, the counting value a is incremented by 1 in step S23 and, subsequently, a is multiplied by a "forget factor" 1-$\epsilon$, which is slightly less than 1. If the compressor 14 is not switched on, the method passes on directly from S22 to S24.

Subsequently, the counting value a is compared with the limit value A. If a is smaller than the limit value A, the warning signal remains switched off, and the method returns to S22; if a is greater than the limit value A, the warning signal is switched on and the method, likewise, returns to S22. In the case of this embodiment of the method, it may happen that, when the thickness of the ice on the evaporator has reached a critical value, the warning signal is, at first, only switched on toward the end of a running time phase of the compressor and goes out again in a subsequent standstill phase. As the thickness of the ice increases, the time periods in which the warning signal is switched on become increasingly long, until it finally remains switched on continuously.

The step S26 may also be omitted; then, the warning signal remains permanently switched on as soon as the counting value a has exceeded the limit value A for the first time.

In a further development of this refinement, a sensor (not illustrated in FIG. 5) analogous to the sensor 11 from FIG. 2 is connected to the control circuit, and the control circuit calculates, as represented in FIG. 4, a humidity factor H and, in step S23, the counting value is incremented by H.

In a further refinement of the invention, the measuring circuit 8 is provided to evaluate measuring signals of one or more sensors that are disposed directly on the evaporator 2 to sense the thickness of the ice on the evaporator 2. Examples of such sensors are schematically represented in FIGS. 7 and 8.

Figure 7:
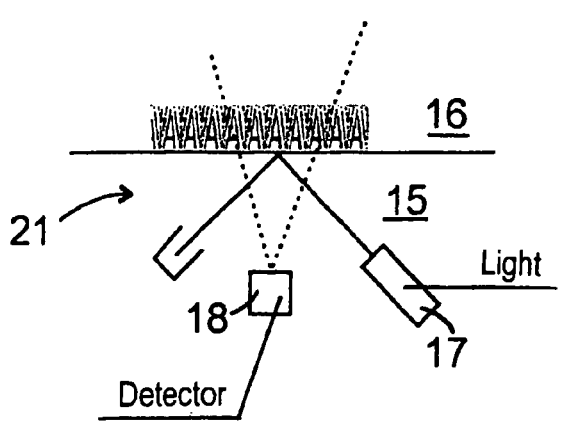
FIG. 7 is a fragmentary, diagrammatic representation of an optical ice sensor according to the invention.

The sensor 21 of FIG. 7 has a transparent body 15 with a surface 16 that is disposed on the evaporator 2 such that it freezes over with ice together with the evaporator 2. A light source 17 and a photodetector 18 are disposed behind the surface 16 such that a light beam emitted from the light source 17 and reflected at the surface 16 does not impinge on the photodetector 18. The reflection is the most intense when the surface 16 is free of ice. If a layer of ice 19 forms on the surface 16, light is diffracted into the layer of ice and diffusely scattered in it. This scattered light is sensed by photodetector 18; the thickness of the layer of ice 19 can be concluded at least approximately from an intensity of the scattered light.

Figure 8:
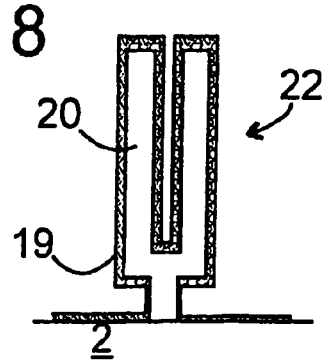
FIG. 8 is a fragmentary, diagrammatic representation of an acoustic ice sensor according to the invention.

The sensor 22 of FIG. 8 includes a resonator 20, which can be electrically induced to vibrate and is disposed on the evaporator 2 such that it freezes over with ice together with the evaporator 2. The resonant frequency of the resonator 20 depends on its mass and, consequently, on the quantity of the ice 19 attached to it. The resonant frequency, consequently, allows the thickness of the ice to be concluded.

We claim:

1. An apparatus for determining and indicating when to defrost a static freezer, said apparatus comprising:
    at least one of a housing having a refrigerating surface that periodically freezes during operation and an evaporator that periodically freezes during freezer operation, forming a layer of ice thereon;
    a sensor for mounting to a predetermined location on the static freezer for substantially continuously measuring whether a predetermined limit quantity of ice has formed at a predetermined location within the static freezer, and being configured to emit a signal when ice has accumulated to said limit, said ice thickness reaching said limit being indicative of the need to commence a manual defrosting procedure; and
    a warning device in communication with said sensor and configured to emit a warning responsive to said signal indicating ice has formed to said limit;
    wherein said sensor has a transparent body with a surface disposed on the refrigerating surface or evaporator such that it freezes over with ice together with the refrigerating surface or evaporator, a light source and a photodetector disposed behind the surface such that a light beam emitted from the light source and reflected at the surface does not impinge on the photodector when the surface is free of ice, whereby if a layer of ice forms on the surface, light is diffracted into the layer of ice and diffusely scattered in it such that the scattered light is sensed by the photodetector in a manner wherein the thickness of the layer of ice can be determined from the intensity of the scattered light.

2. A static freezer having no means for automatic defrosting, comprising:
    a housing having a refrigerating surface that at least periodically freezes during operation;
    a compressor; and
    a measuring circuit programmed to estimate a quantity of ice on said refrigerating surface and supplying a warning signal when an estimated quantity of ice exceeds a predetermined limit value, said measuring circuit having a counter for initializing a counting value for estimating a quantity of ice based upon a ratio of a running time of said compressor to one of:
    a standstill time of said compressor; and
    an overall operating time of the freezer;
    to a value below a predetermined limit value, whereby if the compressor is on, the counting value is incremented by one and then multiplied by a value less than one and wherein the counting value is compared with the predetermined limit value such that if smaller than the predetermined limit value, the warning signal remains off, and if greater than the predetermined limit value, the warning signal is only turned on during a running phase of the compressor and off in a standstill phase until, as the ice increases, a level is reached wherein the warning signal remains switched on continuously.

* * * * *